(12) United States Patent
Cho et al.

(10) Patent No.: US 6,508,935 B2
(45) Date of Patent: Jan. 21, 2003

(54) METHOD AND APPARATUS FOR DETERMINING MEMBRANE PORE SIZE DISTRIBUTION

(75) Inventors: Jaeweon Cho, Kwangju (KR); Sangyoup Lee, Koyang-si (KR); Youngho Cho, Seoul (KR)

(73) Assignee: Kwangju Institute of Science & Technology (KR)

( * ) Notice: Subject to any disclaimer, the term of this patent is extended or adjusted under 35 U.S.C. 154(b) by 24 days.

(21) Appl. No.: 09/863,147

(22) Filed: May 22, 2001

(65) Prior Publication Data

US 2002/0060187 A1 May 23, 2002

(30) Foreign Application Priority Data

Nov. 22, 2000 (KR) .......................................... 2000-69592

(51) Int. Cl.[7] .............................................. B01D 61/00
(52) U.S. Cl. ............................ 210/649; 210/656; 73/38
(58) Field of Search ................................ 210/634, 649, 210/656, 198.2; 73/38

(56) References Cited

U.S. PATENT DOCUMENTS

| | | | | | |
|---|---|---|---|---|---|
| 4,713,975 A | * | 12/1987 | Tomalia | ........................ | 73/38 |
| 4,718,270 A | * | 1/1988 | Storr | ............................ | 73/38 |
| 5,457,986 A | * | 10/1995 | Dileo | ............................ | 73/38 |
| 5,576,480 A | * | 11/1996 | Hopkins | ........................ | 73/38 |
| 5,581,017 A | * | 12/1996 | Bejtlich | ........................ | 73/38 |
| 5,786,528 A | * | 7/1998 | Dileo | ............................ | 73/38 |

* cited by examiner

*Primary Examiner*—Ernest G. Therkorn
(74) *Attorney, Agent, or Firm*—Anderson Kill & Olick, P.C.

(57) ABSTRACT

Described in the present invention are a method for determining the pore size distribution of a membrane filter based on the molecular mass distribution curve of the rejected solute fraction of a feed solution when the feed is passed through the membrane, and an apparatus suitable for practicing said method.

3 Claims, 6 Drawing Sheets

METHOD AND APPARATUS FOR DETERMINING MEMBRANE PORE SIZE DISTRIBUTION

FIELD OF THE INVENTION

The present invention relates to a method for determining the pore size distribution of a membrane filter by way of establishing and analyzing the molecular mass distribution curve of the solute fraction in a feed solution that was rejected by the membrane filtration, and an apparatus therefore.

BACKGROUND OF THE INVENTION

Many kinds of membrane filters, e.g., microfiltration, ultrafiltration and nanofiltration membranes, are used in various water treatment, chemical and food-related processes, and in each application, an accurate membrane pore size measurement is required in order to select a suitable membrane.

Hitherto, the membrane pore size and distribution have been usually measured using electron microscope photography, atomic force microscopy, a liquid displacement method and the like.

Both the electron microscope photography and the liquid displacement method have the disadvantage that they are difficult to apply to ultrafiltration and nanofiltration membranes having small pores. Further, like the electron microscope photography, the atomic force microscopy which measures the membrane pore size using a tip of about 10 nm in diameter has the problem that it is not possible to continuously measure the pore size distribution. Also, these conventional methods all require expensive equipments and cannot be used in determining the pore size of a membrane under the condition of its practical use.

SUMMARY OF THE INVENTION

Accordingly, it is an object of the present invention to provide a simple method for continuously monitoring the pore size distribution of a membrane of any type.

It is another object of the present invention to provide an apparatus which is suitable for practicing the method.

In accordance with one aspect of the present invention, there is provided a method for determining the pore size distribution of a membrane, which comprises passing an aquous solution containing nonionic or charged solutes (feed) through the membrane to obtain a filtrate, measuring relative molecular mass distributions of solutes in the feed and the filtrate which are used to assess the molecular mass distribution curve of the solute fraction rejected by the filtration, and calculating the pore size distribution of the membrane based on said distribution curve.

In accordance with another aspect of the present invention, there is provided an apparatus for determining the pore size distribution of a membrane, which comprises a membrane filtration unit with a membrane holder, means for conducting HPLC (High Performance Liquid Chromatography) and SEC (Size Exclusion Chromatography) to measure molecular mass distributions of solutes in the feed and the filtrate, and a software which analyzes the molecular mass distribution results to obtain the pore size distribution of the membrane.

BRIEF DESCRIPTION OF THE DRAWINGS

The above and other objects and features of the present invention will become apparent from the following description of the invention, when taken in conjunction with the accompanying drawings, which respectively show.

DETAILED DESCRIPTION OF THE INVENTION

Figure 1:
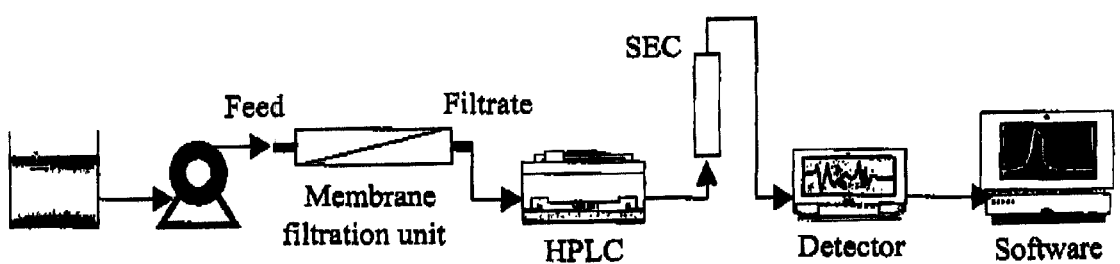
FIG. 1: schematic diagram of an apparatus in accordance with the present invention, for determining the pore size distribution of a membrane.

FIG. 1 represents a schematic diagram of the apparatus of the present invention for determining the pore size distribution of a membrane, and it comprises a membrane filtration unit, HPLC, SEC, a detector and a software for analyzing the results. An aquous solution containing nonionic or charged solutes (feed) is filtered through the membrane held in the membrane filtration unit, and the relative molecular mass distributions of solutes in the feed and the filtrate are measured (HPLC and SEC). Then, the molecular mass distribution of the solute fraction rejected by the filtration (fractional rejection) is assessed and the result was used to determine the membrane pore size distribution using the software.

The feed used in the present invention may be prepared by, for example, dissolving nonionic or charged solutes in ultrapure distilled water obtained by passing distilled water through an activated carbon column, an ion exchange resin and a reverse osmotic membrane filter. A membrane sample whose pore size distribution is to be determined may be dipped in ultrapure distilled water at a low temperature (e.g., 5□) for a predetermined time period (e.g., 12 hours) before use.

In the filtration unit of the present invention, one of two different membrane holders may be employed depending on the type of the membrane, polymeric or ceranic. After a membrane is inserted in an appropriate holder, a feed is passed through the filtration unit to obtain a filtrate which contains solutes passed through the membrane pore.

Exemplary charged macromolecular solutes which may be employed in the present invention include polystyrene sulfonates, salysillic acids, amino acids, natural organic matters (e.g., humic acid and pubic acid) and mixtures thereof. As such charged solutes bear negatively-charged groups which repulsively interact with the negatively charged membrane surface, an effective (as opposed to intrinsic) pore size distribution is obtained as a result.

Exemplary nonionic macromolecular solutes which may be employed in the present invention include polyethylene glycols, polysaccharides and mixtures thereof, and when such nonionic solutes are used, the intrinsic pore size distribution of the membrane is obtained.

Further, in the present invention, various factors, e.g., the type of solutes, pH and ionic strength of the feed, that may affect the effective pore size distribution can be evaluated.

For instance, by way of changing the ion strength of the feed by the addition of sodium chloride or calcium ion, their expected influences on the effective membrane pore size can be assessed in advance.

The molecular mass distribution of solutes contained in the feed or the filtrate is measured with HPLC and SEC. As the eluent of HPLC, ultrapure distilled water is used for nonionic solutes, and a phosphoric acid buffer solution, for charged solutes. In carrying out SEC, a refractive index detector is used for nonionic solutes, and an ultraviolet detector, for charged solutes. The molecular mass distribution of solutes is assessed using a predetermined calibration curve obtained from the correlations between various known molecular masses and their SEC retention times.

Then, in accordance with the present invention, fractional rejection ($R_{Mi}$) of solutes, the solute fraction having a particular molecular mass which did not permeate through the membrane, is calculated using the following equation:

$$R_{Mi} = [W_{Mi} - W'_{Mi}(1 - R_{overall})]/W_{Mi}$$

wherein, $R_{overall}$ is the overall amount of dissolved organic carbons rejected by the membrane filtration, and $W_{Mi}$ and $W'_{Mi}$ are the SEC peak intensities at a particular molecular mass determined for the feed and the filtrate, respectively.

Then, a fractional rejection curve is constructed by plotting $R_{Mi}$ value against the relative molecular mass (X-axis), which exhibits a cut-off value, and molecules having molecular masses larger than this cut-off value cannot pass through the membrane. Also, the shape of the fractional rejection curve is directly related to the pore size distribution of the membrane and such a pore size distribution is obtainable using the software of the present invention.

As described above, the method of the present invention provides a simple and economical means for continuously monitoring the pore size distribution of a membrane of any type under any condition, and, it is particularly usefull in measuring the effective pore size distribution of a membrane in actual use.

The following Examples are given for the purpose of illustration only, and are not intended to limit the scope of the invention.

EXAMPLE 1
Absolute Pore Size Distribution of Polymeric Membrane

A polymeric ultrafiltration membrane having a molecular weight cutoff (MWCO) value of 8000 (provided by the manufacturer) was dipped in ultrapure distilled water at 5□ for 12 hours before use. The ultrapure distilled water was obtained by passing distilled water through an activated carbon column, an ion exchange resin and a reverse osmotic membrane filter. 50 mg of polyethylene glycol (Aldrich, U.S.) having a relatively wide molecular weight range and an average molecular mass of 8000 was dissolved in 1 L of ultrapure distilled water to prepare a polyethylene glycol solution (Solution (A)). Solution (B) and Solution (C) were prepared by adding sodium chloride and calcium ion, respectively, to Solution (A) to a concentration of 10 mM.

Using the apparatus of the present invention shown in FIG. 1, the membrane was inserted in the holder of the filtration unit, and then each of Solution (A), (B) and (C) was introduced to the unit to obtain respective filtrates. Ultrapure distilled water was used as the eluent of HPLC and a refractive index detector was used in SEC (Waters, U.S.). Each of 10 mg portions of polyethylene glycols having average molecular masses of 200, 600, 2000, 3400, 4600 and 8000, respectively, was dissolved in 50 mL of ultrapure distilled water, and these standard polyethylene glycol solutions were used to establish a standard calibration curve.

Figure 2A:
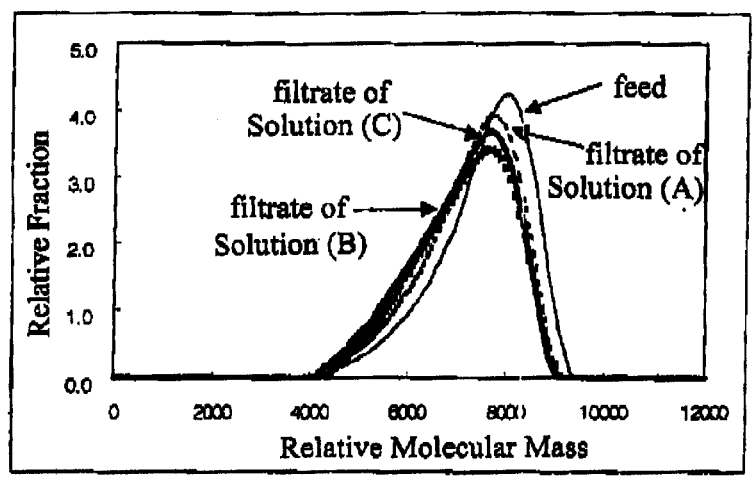
FIGS. 2A to 2C: molecular mass distribution curves of solutes, fractional rejection curves of solutes and absolute pore size distribution curves, respectively, on a polymeric membrane in Example 1.
Figure 2B:
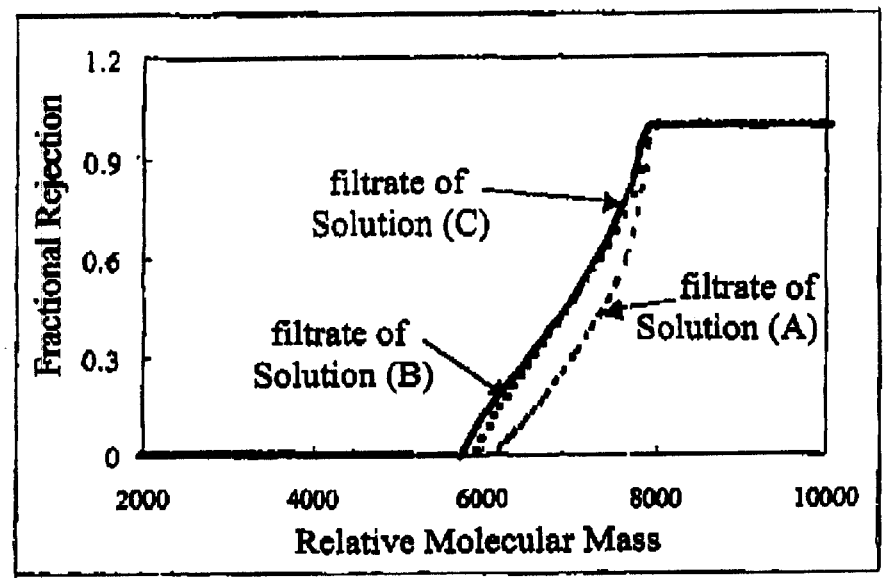
Figure 2C:
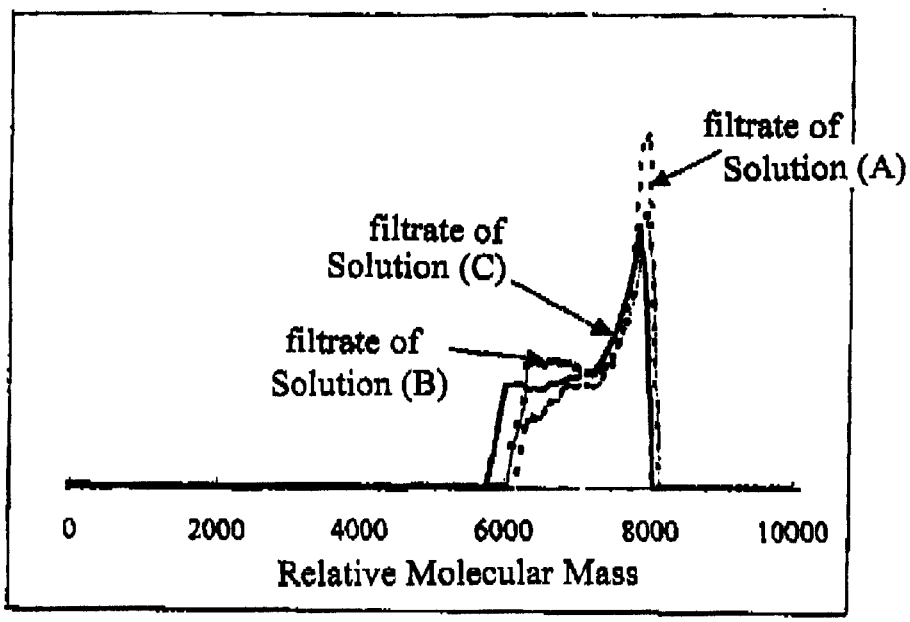

FIG. 2A shows the molecular mass distribution curves of solutes obtained for the feed and the filtrates; FIG. 2B, fractional rejection curves of solutes calculated from the curves of FIG. 2A; and FIG. 2C, absolute membrane pore size distribution curves deduced from the curves of FIG. 2B. As shown in FIGS. 2A to 2C, the addition of sodium chloride which increases the ionic strength of the feed, or the addition of calcium ion which results in a decrease in the charge repulsive interaction of the feed, brings about a decrease in the effective pore size of the membrane.

EXAMPLE 2
Absolute Pore Size Distribution of Polymeric Membrane

The procedure of Example 1 was repeated using polyethylene glycol having a relatively wide molecular weight range and an average molecular mass of 250 together with a polymeric nanofiltration membrane whose molecular weight cutoff (MWCO) value is 250 (provided by the manufacturer).

Figure 3:
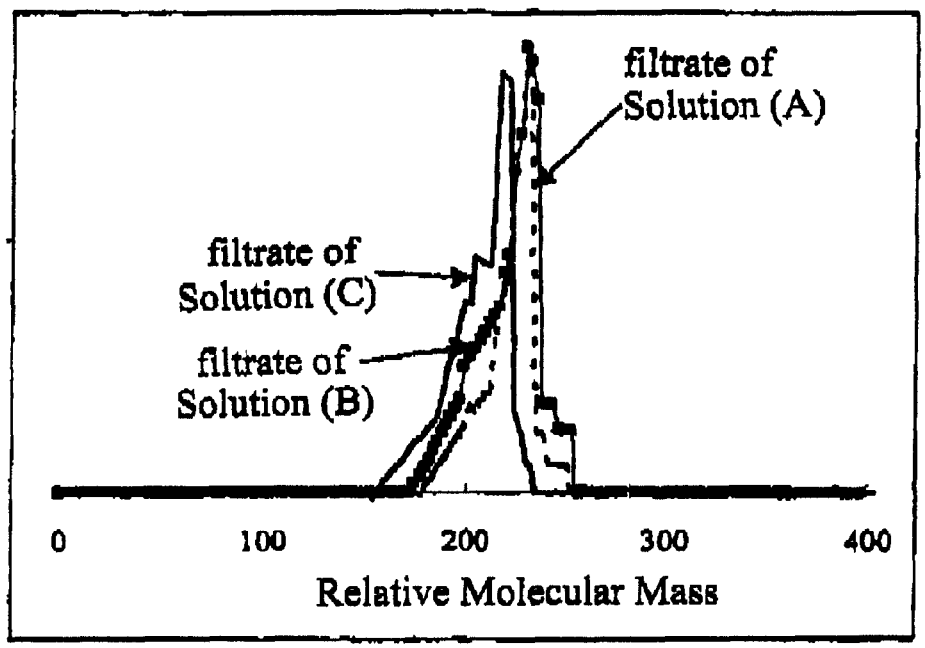
FIG. 3: absolute pore size distribution curves on a polymeric membrane in Example 2.
Figure 4:
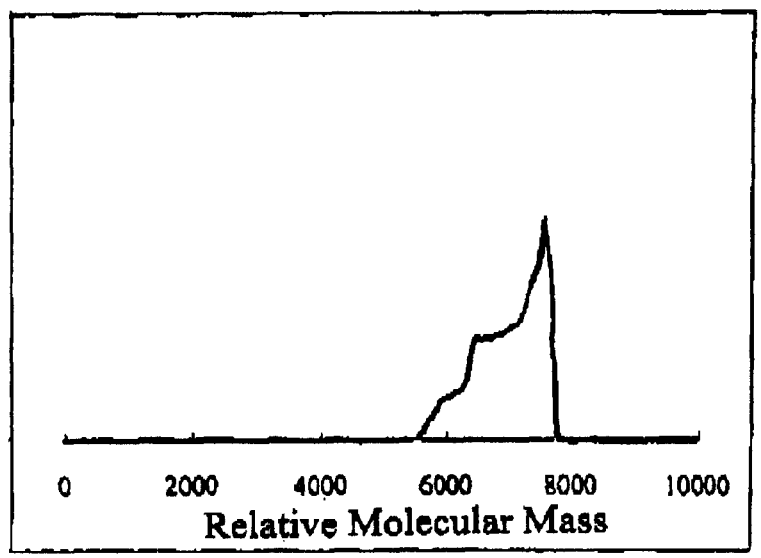
FIGS. 4 to 7: absolute pore size distribution curves on respective ceramic membranes in Examples 3 to 6.
Figure 5:
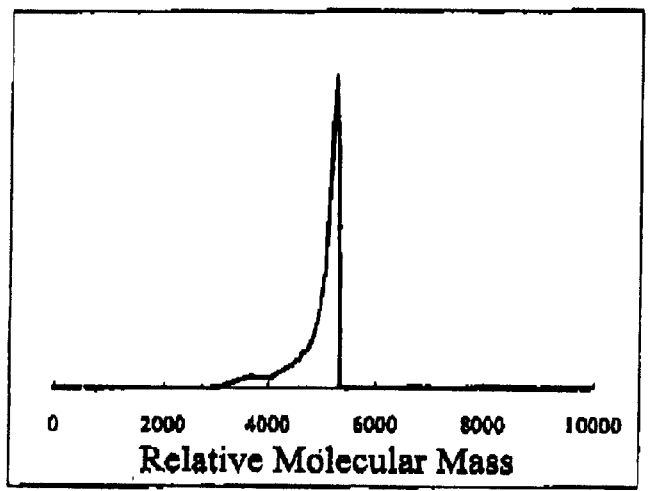
Figure 6:
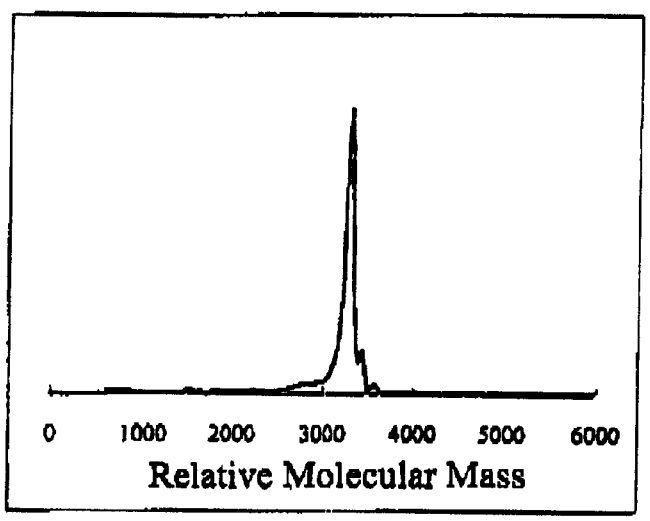
Figure 7:
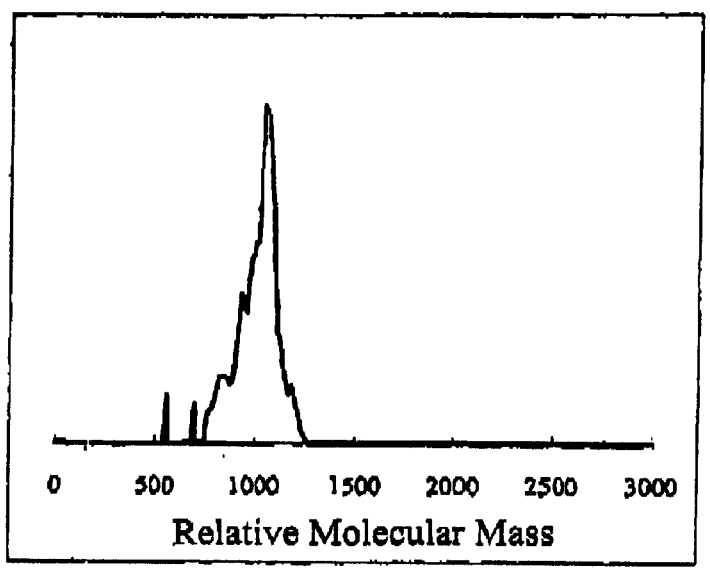

FIG. 3 exhibits the absolute membrane pore size distribution curves thus obtained. As shown in FIG. 3, the addition of sodium chloride which increases the ionic strength of the feed, or the addition of calcium ion which results in a decrease in the charge repulsive interaction of the feed, brings about a decrease in the effective pore size of the membrane.

EXAMPLES 3 TO 6
Intrinsic Pore Size Distributions of Ceramic Membranes

The procedure of Example 1 was repeated using polyethylene glycols having relatively wide molecular weight ranges and average molecular masses of 8000, 5000, 3000 and 1000, respectively, together with ceramic titanium oxide membranes whose molecular weight cutoff (MWCO) values are 8000, 5000, 3000 and 1000, respectively (provided by the manufacturer).

FIGS. 4 to 7 show the respective intrinsic membrane pore size distribution curves thus obtained.

EXAMPLE 7
Effective Pore Size Distribution of Polymeric Membrane

A polymeric ultrafiltration membrane having a molecular weight cutoff (MWCO) value of 8000 (provided by the manufacturer) was dipped in ultrapure distilled water at 5□ for 12 hours before use. A Nakdong River surface water sample was taken at the Bansong water treatment plant, Changwon City (Korea), immediately filtered through a 0.45□ filter and then used as the feed.

Using the apparatus of the present invention shown in FIG. 1, the membrane was inserted in the holder of the filtration unit, and then the feed was introduced to the unit to obtain a filtrate. A phosphoric acid buffer solution having pH 6.8 and an ion strength of 0.1M was used as the eluent of HPLC and an ultraviolet detector was used in SEC (Waters, U.S.). Each of 10 mg portions of polystyrene sulfonates having average molecular masses of 1800, 4600, 8000 and 35000, respectively, was dissolved in 50 mL of ultrapure distilled water, and these standard polystyrene sulfonate solutions were used to establish a standard calibration curve.

Figure 8A:
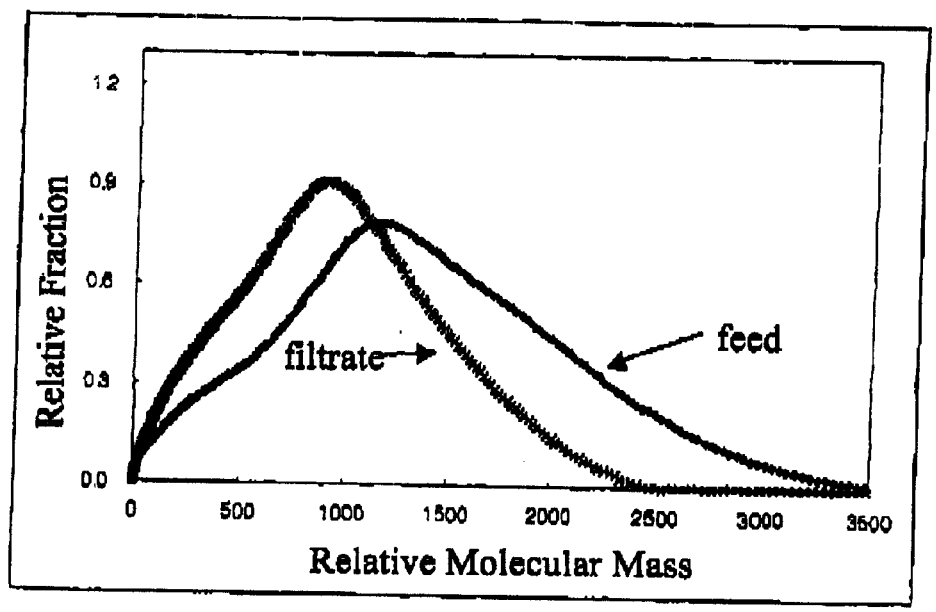
FIGS. 8A and 8B: molecular mass distribution curves of solutes and effective pore size distribution curve, respectively, on a polymeric membrane in Example 7.
Figure 8B:
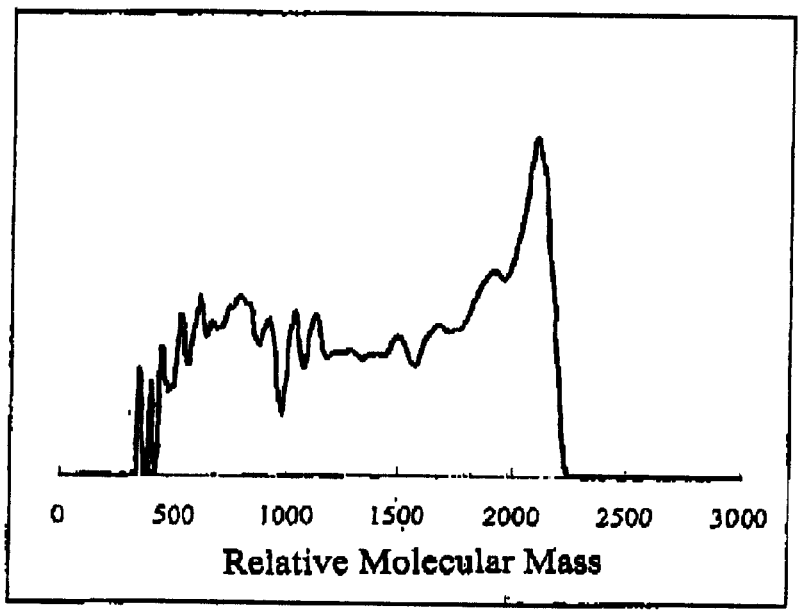

FIG. 8A depicts the molecular mass distribution curves of solutes (natural organic matters) obtained for the feed and the filtrate; and FIG. 8B, effective pore size distribution curve of the membrane. As shown in FIGS. 8A and 8B, the measured value of the effective membrane pore size is smaller than 8000, the value provided by the manufacturer. This may be attributable to the charge repulsion interaction between charged natural organic matters in the feed and the membrane surface.

EXAMPLE 8
Effective Pore Size Distribution of Polymeric Membrane

The procedure of Example 7 was repeated using a polymeric nanofiltration membrane with a molecular weight cutoff (MWCO) value of 250 (provided by the manufacturer).

Figure 9:
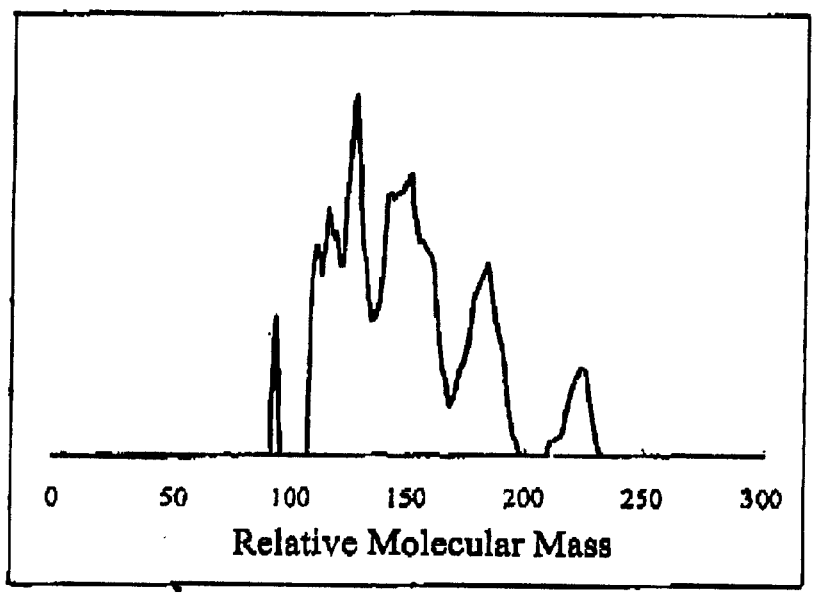
FIG. 9: effective pore size distribution curve on a polymeric membrane in Example 8.

As shown in FIG. 9, the measured value of the effective membrane pore size is smaller than 250, the value provided by the manufacturer. This may be attributable to the charge repulsion interaction between charged natural organic matters in the feed and the membrane surface.

As described above, in accordance with the method of the present invention, the pore size distribution of a membrane of any type can be determined economically and continuously, under the condition of its practical use.

While the embodiments of the subject invention have been described nd illustrated, it is obvious that various changes and modifications can be ade therein without departing from the spirit of the present invention which should be limited only by the scope of the appended claims.

What is claimed is:

1. A method for determining the pore size distribution of a membrane, which comprises passing an aquous solution containing nonionic or charged solutes (feed) through the membrane to obtain a filtrate, chromatographically measuring relative molecular mass distributions of solutes in the feed and the filtrate which are used to assess the molecular mass distribution curve of the solute fraction rejected by the filtration, and calculating the pore size distribution of the membrane based on said distribution curve.

2. The method of claim 1, wherein charged solutes are selected from the group consisting of polystyrene sulfonates, salysillic acids, amino acids, natural organic matters and mixtures thereof.

3. The method of claim 1, wherein nonionic solutes are selected from the group consisting of polyethylene glycols, polysaccharides and mixtures thereof.

* * * * *